US010221109B2

(12) United States Patent
Toda et al.

(10) Patent No.: US 10,221,109 B2
(45) Date of Patent: Mar. 5, 2019

(54) METHOD FOR PRODUCING ALPHA-OLEFIN LOW POLYMER

(71) Applicant: MITSUBISHI CHEMICAL CORPORATION, Chiyoda-ku (JP)

(72) Inventors: Satoshi Toda, Okayama (JP); Hiroki Emoto, Okayama (JP)

(73) Assignee: MITSUBISHI CHEMICAL CORPORATION, Chiyoda-ku (JP)

(*) Notice: Subject to any disclaimer, the term of this patent is extended or adjusted under 35 U.S.C. 154(b) by 0 days.

(21) Appl. No.: 15/245,772

(22) Filed: Aug. 24, 2016

(65) Prior Publication Data

US 2016/0362350 A1     Dec. 15, 2016

Related U.S. Application Data

(63) Continuation of application No. PCT/JP2015/055304, filed on Feb. 24, 2015.

(30) Foreign Application Priority Data

Feb. 25, 2014  (JP) .................................. 2014-034394
Mar. 24, 2014  (JP) .................................. 2014-060711

(51) Int. Cl.
    *C07C 2/32*      (2006.01)
    *C08F 210/16*    (2006.01)
(52) U.S. Cl.
    CPC ............. *C07C 2/32* (2013.01); *C08F 210/16* (2013.01); *C07C 2531/14* (2013.01); *C07C 2531/16* (2013.01); *C07C 2531/22* (2013.01)
(58) Field of Classification Search
    None
    See application file for complete search history.

(56) References Cited

U.S. PATENT DOCUMENTS

| 5,856,612 A | 1/1999 | Araki et al. |
| 5,910,619 A | 6/1999 | Urata et al. |

(Continued)

FOREIGN PATENT DOCUMENTS

| CN | 1182729 A   | 5/1998 |
| CN | 101547941 A | 9/2009 |

(Continued)

OTHER PUBLICATIONS

International Search Report dated May 26, 2015 in PCT/JP2015/055304, filed on Feb. 24, 2015 ( with English Translation).
Written Opinion dated May 26, 2015 in PCT/JP2015/055304, filed on Feb. 24, 2015.
Combined Office Action and Search Report dated Nov. 1, 2017 in Taiwanese Patent Application No. 104106024 (with English translation).

(Continued)

*Primary Examiner* — Philip T Louie
(74) *Attorney, Agent, or Firm* — Oblon, McClelland, Maier & Neustadt, L.L.P.

(57) ABSTRACT

The present invention relates to a method for producing an α-olefin low polymer through low polymerization reaction of an α-olefin in the presence of a catalyst containing a transition metal-containing compound, an aluminum-containing compound and a hydrocarbon having 2 or more carbon atoms and substituted with a halogen atom, and a solvent, which comprises a reaction step, a purification step and a circulation step of circulating the unreacted raw material α-olefin and the solvent from the purification step to the reaction step; and in which the amount of the olefin having 2 or more carbon atoms and substituted with a halogen atom that is supplied from the circulation step to the reaction step is within a range of from 0.1 to less than 200 (molar ratio) relative to the amount of the transition metal in the reaction step.

12 Claims, 1 Drawing Sheet

(56) References Cited

U.S. PATENT DOCUMENTS

| | | | |
|---|---|---|---|
| 9,272,961 B2 | 3/2016 | Emoto et al. | |
| 2003/0100688 A1* | 5/2003 | Farrer | C08F 10/00 526/110 |
| 2009/0326297 A1* | 12/2009 | Emoto | B01J 31/143 585/530 |
| 2010/0331503 A1 | 12/2010 | Emoto et al. | |

FOREIGN PATENT DOCUMENTS

| | | |
|---|---|---|
| CN | 102417554 A | 4/2012 |
| JP | 8-134131 | 5/1996 |
| JP | 9-143213 | 6/1997 |
| JP | 9-268135 | 10/1997 |
| JP | 9-268136 | 10/1997 |
| JP | 10-109946 | 4/1998 |
| JP | 2008-179801 | 8/2008 |
| RU | 2011135580 A | 2/2013 |

OTHER PUBLICATIONS

Office Action dated Jan. 22, 2018, in Russian Patent Application No. 2016134442 (w/ English translation).
Office Action dated Jan. 23, 2018, in Japanese Patent Application No. 2015-024274 (w/ computer-generated English translation).
Office Action dated Mar. 12, 2018, in Chinese Patent Application No. 201580010235.1 (w/ English translation).
Office Action dated Jul. 31, 2018, in Japanese Patent Application No. 2015-024274 (w/ Computer-generated English translation).
Office Action dated Nov. 15, 2018, in Chinese Patent Application No. 201580010235.1 (w/ English translation).
Office Action dated Dec. 12, 2018, in Indian Patent Application No. 201617028942 (w/ English translation).
Examination Report prepared Dec. 6, 2018 and dated Dec. 31, 2018 in GCC Patent Application No. GC 2015-28979.

* cited by examiner

METHOD FOR PRODUCING ALPHA-OLEFIN LOW POLYMER

TECHNICAL FIELD

The present invention relates to a method for producing an α-olefin low polymer through low polymerization reaction of an α-olefin in a solvent in the presence of a catalyst, and more specifically, to a method for producing 1-hexene through low polymerization reaction of a raw material ethylene.

An α-olefin low polymer is a useful substance widely used as a raw material for a monomer for an olefinic polymer, as a comonomer for various polymers, and also as a raw material for plasticizers, surfactants, lubricating oils, etc. In particular, 1-hexene to be produced through low polymerization reaction of ethylene is useful as a raw material for a linear low-density polyethylene.

BACKGROUND ART

In general, an α-olefin low polymer is produced according to a method of low polymerization reaction of an α-olefin in the presence of a catalyst and a solvent. For example, JP-A 8-134131 discloses a method for producing 1-hexene through trimerization of ethylene in the presence of a catalyst containing a chromium compound and a halogen-containing compound and a solvent, and discloses halides of linear hydrocarbons as the halogen-containing compound (PTL 1).

JP-A 2008-179801 discloses that 1-hexene as a raw material for polyethylene production, which is produced through trimerization of ethylene in the presence of a catalyst containing a chromium compound and a halogen-containing compound contains a halogenated olefin that is generated as a side product in decomposition of the halogen-containing compound (PTL 2).

BACKGROUND ART DOCUMENT

Patent Literature

[PTL 1] JP-A 8-134131
[PTL 2] JP-A 2008-179801

SUMMARY OF INVENTION

Problem that Invention is to Solve

In industrial-scale production of an α-olefin low polymer such as 1-hexene or the like using an α-olefin such as ethylene or the like as a raw material, further improvement in the selectivity of the intended product is desired, and the already-existing technology is desired to be further improved in point of the selectivity. At the start of production operation, the production selectivity of the intended product as well as the intended product purity is low, and especially it has been necessary to improve the intended product impurity relating to product quality.

An object of the present invention is to provide a production method for an α-olefin low polymer through low polymerization reaction of an α-olefin, especially a production method for 1-hexene through trimerization of ethylene, and to provide a production method for an α-olefin low polymer capable of improving the selectivity of the intended product while maintaining the activity to fall within an acceptable range, or that is, to provide an industrially-advantageous production method for an α-olefin low polymer.

Means for Solving Problem

The present inventors have assiduously studied for the purpose of solving the above-mentioned problems and, as a result, have found that, in case where a hydrocarbon having 2 or more carbon atoms and substituted with a halogen atom is used as a halogen-containing compound which is one component of a chromium-based homogeneous catalyst, and when a specific amount of the olefin having 2 or more carbon atoms and substituted with a halogen atom of the decomposed product is circulated in the reactor, then the selectivity of the intended product can be improved. In addition, the inventors have further found that, when the reaction is started in the condition where an olefin having 2 or more carbon atoms and substituted with a halogen atom is made to exist within a specific range in the circulation step at the start of the production operation, then the selectivity and the purity of the intended product can be improved from the start of the reaction, and have completed the present invention.

Specifically, the gist of the present invention resides in the following [1] to [9].

[1] A method for producing an α-olefin low polymer through low polymerization reaction of an α-olefin in the presence of a catalyst containing a transition metal-containing compound, an aluminium-containing compound and a hydrocarbon having 2 or more carbon atoms and substituted with a halogen atom, and a solvent, which comprises:

a reaction step, a purification step and a circulation step of circulating the unreacted raw material α-olefin and the solvent from the purification step to the reaction step; and wherein:

the amount of the olefin having 2 or more carbon atoms and substituted with a halogen atom that is supplied from the circulation step to the reaction step is within a range of from 0.1 to less than 200 (molar ratio) relative to the amount of the transition metal in the reaction step.

[2] The method for producing an α-olefin low polymer described in the above [1], wherein the catalyst further contains a nitrogen-containing compound as the constitutive component.

[3] The method for producing an α-olefin low polymer described in the above [1] or [2], wherein the transition metal is chromium.

[4] The method for producing an α-olefin low polymer described in any one of the above [1] to [3], wherein the α-olefin is ethylene and the α-olefin low polymer is 1-hexene.

[5] The method for producing an α-olefin low polymer described in any one of the above [1] to [4], wherein the reaction is started in the condition where an olefin having 2 or more carbon atoms and substituted with one or more halogen atoms is made to exist in the circulation step within a range of from 0.1 to less than 200 (molar ratio) relative to the amount of the transition metal in the reaction step, at the start of the production operation.

[6] The method for producing an α-olefin low polymer described in any one of the above [1] to [5], wherein the amount of the olefin having 2 or more carbon atoms and substituted with a halogen atom is within a range of from 0.1 to 170 (molar ratio) relative to the amount of the transition metal in the reaction step.

[7] The method for producing an α-olefin low polymer described in any one of the above [1] to [6], wherein the hydrocarbon having 2 or more carbon atoms and substituted with a halogen atom is a hydrocarbon having 2 or more carbon atoms and substituted with 5 or more halogen atoms, and the olefin having 2 or more carbon atoms and substituted with a halogen atom is an olefin having 2 or more carbon atoms and substituted with 3 or more halogen atoms.

[8] The method for producing an α-olefin low polymer described in any one of the above [1] to [6], wherein the hydrocarbon having 2 or more carbon atoms and substituted with a halogen atom is 1,1,2,2-tetrachloroethane, and the olefin having 2 or more carbon atoms and substituted with a halogen atom is 1,2-dichloroethylene.

[9] A method for producing an α-olefin low polymer through low polymerization reaction of an α-olefin in the presence of a catalyst containing a transition metal-containing compound, an aluminium-containing compound and a hydrocarbon having 2 or more carbon atoms and substituted with a halogen atom, and a solvent, wherein:

an olefin having 2 or more carbon atoms and substituted with a halogen atom is supplied in the reaction step within a range of from 0.1 to less than 200 (molar ratio) relative to the amount of the transition metal in the reaction step.

Effects of Invention

According to the present invention, in producing an α-olefin low polymer through low polymerization reaction of an α-olefin, the selectivity of the intended product can be improved while the activity is kept within an acceptable range.

DESCRIPTION OF EMBODIMENTS

Figure 1:
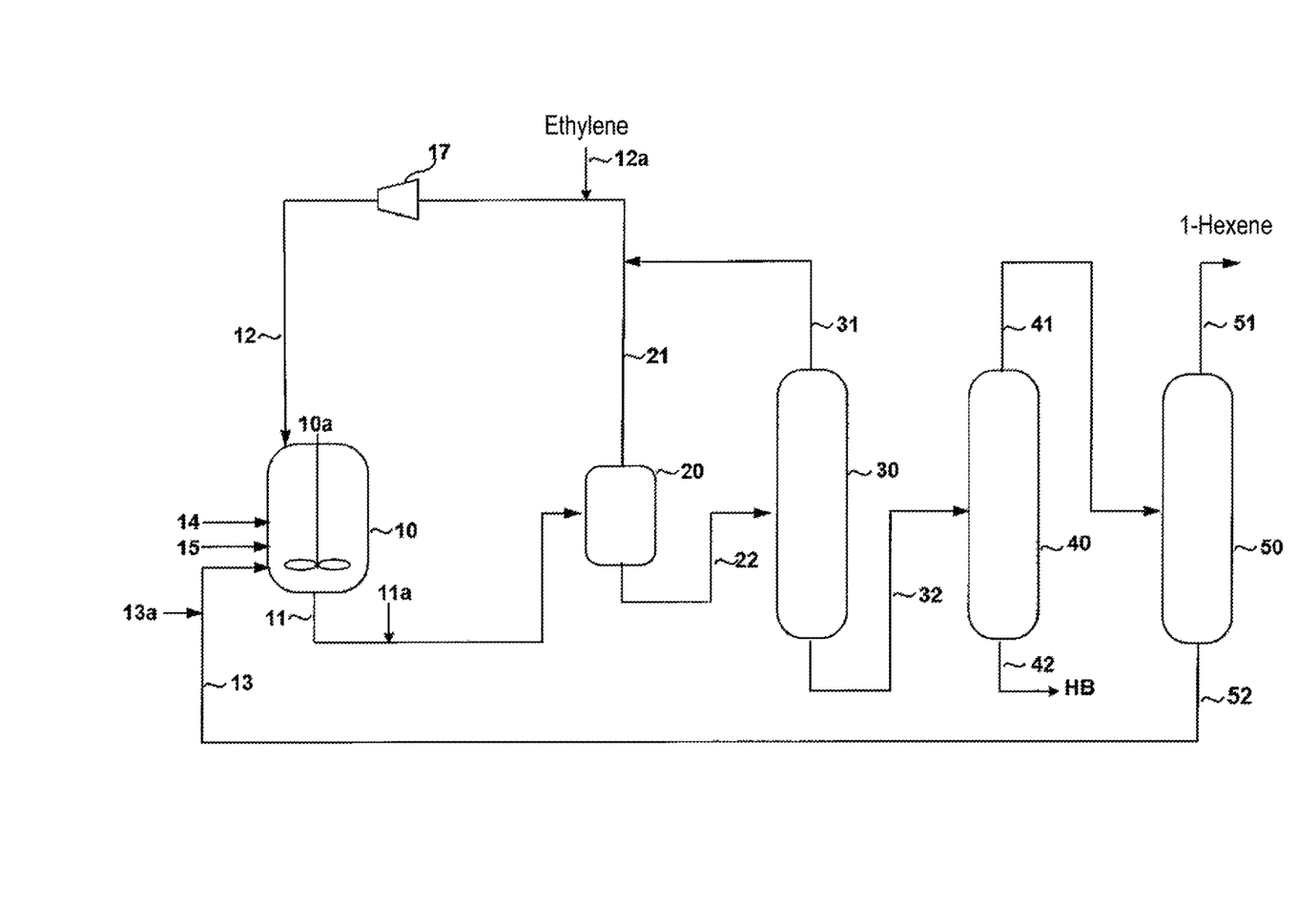
FIGURE is a view for explaining an example of a production flow for an α-olefin low polymer (1-hexene) in one embodiment of the invention.

Best modes for carrying out the present invention (hereinafter, referred to as embodiments of the invention) are described in detail hereinunder. The present invention is not limited to the following embodiments, and can be variously modified and changed within the range of the scope and the spirit thereof.

[Catalyst]

The catalyst for use in the present invention is not specifically limited as long as it is a catalyst which can produce an α-olefin low polymer through low polymerization reaction of a raw material α-olefin, and contains, as the constitutive components of the catalyst, a transition metal-containing compound, an aluminium-containing compound and, as a halogen-containing compound, a hydrocarbon having 2 or more carbon atoms and substituted with a halogen atom. From the viewpoint of improving the catalyst activity, preferably, the catalyst contains a nitrogen-containing compound as the constitutive component of the catalyst.

(Transition Metal-Containing Compound)

In the production method for the α-olefin low polymer of the present invention, the transition metal contained in the transition metal-containing compound which is used as in the catalyst is not specifically limited as long as it is a transition metal. Among these, preferred is a transition metal of Group 4 to Group 6 of the Long Form Periodic Table (hereinunder unless otherwise specifically indicated, "Periodic Table" indicates Long Form Periodic Table). Concretely, preferred are one or more metals selected from chromium, titanium, zirconium, vanadium and hafnium; more preferred is chromium or titanium; and most preferred is chromium.

In the present invention, the transition metal-containing compound to be used as the raw material of the catalyst is one or more compounds represented by $MeZ_n$. Here, in the general formula, Me represents a transition metal element, Z represents an arbitrary organic group or inorganic group or a negative atom, and n indicates an integer of from 1 to 6, and is preferably 2 or more. When n is 2 or more, Z's may be the same or different from each other. The organic group may be a hydrocarbon group having from 1 to 30 carbon atoms and optionally having a substituent and specific examples include a carbonyl group, an alkoxy group, a carboxyl group, a β-diketonate group, a β-ketocarboxyl group, a β-ketoester group, an amide group, etc. Examples of the inorganic group include a metal salt-forming group such as a nitric acid group, a sulfuric acid group, etc. Examples of the negative atom include an oxygen atom, a halogen atom, etc.

Specific examples of the transition metal-containing compound where the transition metal is chromium (hereinafter it may be referred to as a chromium-containing compound) include chromium(IV)-tert-butoxide, chromium(III) acetylacetonate, chromium(III) trifluoroacetylacetonate, chromium(III) hexafluoroacetylacetonate, chromium(III) (2,2,6,6-tetramethyl-3,5-heptanedionate), $Cr(PhCOCHCOPh)_3$ (where Ph represents a phenyl group), chromium(II) acetate, chromium(III) acetate, chromium(III)-2-ethylhexanoate, chromium(III) benzoate, chromium(III) naphthenate, chromium(III) heptanoate, $Cr(CH_3COCHCOOCH_3)_3$, chromous chloride, chromic chloride, chromous bromide, chromic bromide, chromous iodide, chromic iodide, chromous fluoride, chromic fluoride, etc.

Specific examples of the transition metal-containing compound where the transition metal is titanium (hereinafter it may be referred to as a titanium-containing compound) include $TiCl_4$, $TiBr_4$, $TiI_4$, $TiBrCl_3$, $TiBr_2Cl_2$, $Ti(OC_2H_5)_4$, $Ti(OC_2H_5)_2Cl_2$, $Ti(O-n-C_3H_7)_4$, $Ti(O-n-C_3H_7)_2Cl_2$, $Ti(O-iso-C_3H_7)_4$, $Ti(O-iso-C_3H_7)_2Cl_2$, $Ti(O-n-C_4H_9)_4$, $Ti(O-n-C_4H_9)_2Cl_2$, $Ti(O-iso-C_4H_9)_4$, $Ti(O-iso-C_4H_9)_2Cl_2$, $Ti(O-tert-C_4H_9)_4$, $Ti(O-tert-C_4H_9)_2Cl_2$, $TiCl_4(thf)_2$ (in this chemical formula, thf represents tetrahydrofuran), $Ti((CH_3)_2N)_4$, $Ti((C_2H_5)_2N)_4$, $Ti((n-C_3H_7)_2N)_4$, $Ti((iso-C_3H_7)_2N)_4$, $Ti((n-C_4H_9)_2N)_4$, $Ti((tert-C_4H_9)_2N)_4$, $Ti(OSO_3CH_3)_4$, $Ti(OSO_3C_2H_5)_4$, $Ti(OSO_3C_3H_7)_4$, $Ti(OSO_3C_4H_9)_4$, $TiCp_2Cl_2$, $TiCp_2ClBr$, $Ti(OCOC_2H_5)_4$, $Ti(OCOC_2H_5)_2Cl_2$, $Ti(OCOC_3H_7)_4$, $Ti(OCOC_3H_7)_2Cl_2$, $Ti(OCOC_3H_7)_4$, $Ti(OCOC_3H_7)_2Cl_2$, $Ti(OCOC_4H_9)_4$, $Ti(OCOC_4H_9)_2Cl_2$, etc.

Here, Cp represents a cyclopentadienyl group.

Specific examples of the transition metal-containing compound where the transition metal is zirconium (hereinafter it may be referred to as a zirconium-containing compound) include $ZrCl_4$, $ZrBr_4$, $ZrI_4$, $ZrBrCl_3$, $ZrBr_2Cl_2$, $Zr(OC_2H_5)_4$, $Zr(OC_2H_5)_2Cl_2$, $Zr(O-n-C_3H_7)_4$, $Zr(O-n-C_3H_7)_2Cl_2$, $Zr(O-iso-C_3H_7)_4$, $Zr(O-iso-C_3H_7)_2Cl_2$, $Zr(O-n-C_4H_9)_4$, $Zr(O-n-C_4H_9)_2Cl_2$, $Zr(O-iso-C_4H_9)_4$, $Zr(O-iso-C_4H_9)_2Cl_2$, $Zr(O-tert-C_4H_9)_4$, $Zr(O-tert-C_4H_9)_2Cl_2$, $Zr((CH_3)_2N)_4$, $Zr((C_2H_5)_2N)_4$, $Zr((n-C_3H_7)_2N)_4$, $Zr((iso-C_3H_7)_2N)_4$, $Zr((n-C_4H_9)_2N)_4$, $Zr((tert-C_4H_9)_2N)_4$, $Zr(OSO_3CH_3)_4$, $Zr(OSO_3C_2H_5)_4$, $Zr(OSO_3C_3H_7)_4$, $Zr(OSO_3C_4H_9)_4$, $ZrCp_2Cl_2$, $ZrCp_2ClBr$, $Zr(OCOC_2H_5)_4$, $Zr(OCOC_2H_5)_2Cl_2$, $Zr(OCOC_3H_7)_4$, $Zr(OCOC_3H_7)_2Cl_2$, $Zr(OCOC_3H_7)_4$, Zr(OCOC$_3$H$_7$)$_2$Cl$_2$, Zr(OCOC$_4$H$_9$)$_4$, Zr(OCOC$_4$H$_9$)$_2$Cl$_2$, ZrCl$_2$(HCOCFCOF)$_2$, ZrCl$_2$(CH$_3$COCFCOCH$_3$)$_2$, etc.

Specific examples of the transition metal-containing compound where the transition metal is vanadium (hereinafter it may be referred to as a vanadium-containing compound) include vanadium pentoxide, vanadium oxytrichloride, vanadium oxytribromide, methoxy vanadate, ethoxy vanadate, n-propyl vanadate, isopropoxy vanadate, n-butoxy vanadate, isobutoxy vanadate, t-butyl vanadate, 1-methylbutoxy vanadate, 2-methylbutoxy vanadate, n-propoxy vanadate, neopentoxy vanadate, 2-ethylbutyloxy vanadate, cyclohexyl vanadate, allylcyclohexyl vanadate, phenoxy vanadate, vanadium(III) acetylacetonate, vanadium(III) hexafluoroacetylacetonate, vanadium(III) (2,2,6,6-tetramethyl-3,5-heptanedionate), V(C$_6$H$_5$COCHCOC$_6$H$_5$)$_3$, vanadium(III) acetate, vanadium(III) 2-ehtylhexanoate, vanadium(III) benzoate, vanadium(III) naphthenate, V(CH$_3$COCHCOOCH$_3$)$_3$, vanadium(III) chloride, vanadium(III) bromide, vanadium(III) iodide, vanadium(III) fluoride, bis(cyclopentadienyl)vanadiumdimethyl, bis(cyclopentadienyl)vanadiumdimethyl chloride, bis (cyclopentadienyl)vanadiumethyl chloride, bis (cyclopentadienyl)vanadium dichloride, etc.

Specific examples of the transition metal-containing compound where the transition metal is hafnium (hereinafter it may be referred to as a hafnium-containing compound) include dimethylsilylenebis{1-(2-methyl-4-isopropyl-4H-azulenyl)}hafnium dichloride, dimethylsilylenebis{1-(2-methyl-4-phenyl-4H-azulenyl)}hafnium dichloride, dimethylsilylenebis[1-{2-methyl-4-(4-chlorophenyl)-4H-azulenyl}]hafnium dichloride, dimethylsilylenebis[1-{2-methyl-4-(4-fluorophenyl)-4H-azulenyl}]hafnium dichloride, dimethylsilylenebis[1-{2-methyl-4-(3-chlorophenyl)-4H-azulenyl}]hafnium dichloride, dimethylsilylenebis[1-{2-methyl-4-(2,6-dimethylphenyl)-4H-azulenyl}]hafnium dichloride, dimethylsilylenebis{1-(2-methyl-4,6-diisopropyl-4H-azulenyl)}hafnium dichloride, diphenylsilylenebis{1-(2-methyl-4-phenyl-4H-azulenyl)}hafnium dichloride, methylphenylsilylenebis{1-(2-methyl-4-phenyl-4H-azulenyl)}hafnium dichloride, methylphenylsilylenebis[1-{2-methyl-4-(1-naphtyl)-4H-azulenyl}]hafnium dichloride, dimethylsilylenebis{1-(2-ethyl-4-phenyl-4H-azulenyl)}hafnium dichloride, dimethylsilylenebis[1-{2-ethyl-4-(1-anthracenyl)-4H-azulenyl}]hafnium dichloride, dimethylsilylenebis[1-{2-ethyl-4-(2-anthracenyl)-4H-azulenyl}]hafnium dichloride, dimethylsilylenebis[1-{2-ethyl-4-(9-phenanthryl)-4H-azulenyl}]hafnium dichloride, dimethylmethylenebis[1-{2-methyl-4-(4-biphenylyl)-4H-azulenyl}]hafnium dichloride, dimethylgermylenebis[1-{2-methyl-4-(4-biphenylyl)-4H-azulenyl}]hafnium dichloride, dimethylsilylenebis{1-{2-ethyl-4-(3,5-dimethyl-4-trimethylsilylphenyl-4H-azulenyl)}hafnium dichloride, dimethylsilylenebis[1-{2-methyl-4-(4-biphenyl)-4H-azulenyl}][1-{2-methyl-4-(4-biphenylyl)indenyl}]hafnium dichloride, dimethylsilylene{1-(2-ethyl-4-phenyl-4H-azulenyl)}{1-(2-methyl-4,5-benzindenyl)}hafnium dichloride, dimethylsilylenebis{1-(2-methyl-4-phenylindenyl)}hafnium dichloride, dimethylsilylenebis{1-(2-methyl-4,5-benzindenyl)}hafnium dichloride, dimethylsilylenebis[1-(2-methyl-4-(1-naphthyl)indenyl}]hafnium dichloride, etc.

Among those transition metal-containing compounds, preferred are chromium-containing compounds; and among the chromium-containing compounds, especially preferred is chromium(III)-2-ethylhexanoate.

(Aluminium-Containing Compound)

The aluminium-containing compound for use in the present invention is a compound containing an aluminium atom in the molecule, and specific examples include trialkylaluminium compounds, alkoxyalkylaluminium compounds, alkylaluminium hydride compounds, etc. Here, the carbon number of each of the alkyl and the alkoxy is generally from 1 to 20, preferably from 1 to 4. The trialkylaluminium compound includes, for example, trimethylaluminium, triethylaluminium, and triisobutylaluminium. Specific examples of the alkoxyaluminium compound include diethylaluminium ethoxide. Specific examples of the alkylaluminium hydride compound include diethylaluminium hydride. Among these, preferred are trialkylaluminium compounds, and more preferred is triethylaluminium. One alone or two or more of these compounds may be used here either singly or as combined.

(Halogen-Containing Compound)

The halogen-containing compound for use in the present invention is a compound containing a halogen atom in the molecule. In the present invention, used are hydrocarbons each having 2 or more carbon atoms and substituted with a halogen atom. Using the compound provides an advantage of markedly improving the catalyst activity and the intended product selectivity. The halogen-containing compound is preferably a saturated hydrocarbon having 2 or more carbon atoms and substituted with 3 or more halogen atoms.

The halogen atom includes a chlorine atom, a fluorine atom and a bromine atom. Preferred is a chlorine atom since it has a tendency to increase the catalyst activity and the intended product selectivity.

The hydrocarbon having 2 or more carbon atoms and substituted with a halogen atom includes chloroethylene, dichloroethylene, trichloroethane, trichloroethylene, tetrachloroethane, tetrachloro ethylene (perchloroethylene), pentachloroethane, hexachloroethane, fluoroethylene, difluoroethylene, trifluoroethane, trifluoroethylene, tetrafluoroethane, tetrafluoroethylene (perfluoroethylene), pentafluoroethane, hexafluoroethane, bromoethylene, dibromoethylene, tribromoethane, tribromoethylene, tetrabromoethane, tetrabromoethylene (perbromoethylene), pentabromoethane, hexabromoethane, and the compounds mentioned below.

As the saturated hydrocarbon having 2 or more carbon atoms and substituted with 3 or more halogen atoms, preferred for use herein are 1,1,2,2-tetrachloroethane and hydrocarbons having 2 or more carbon atoms and substituted with 5 or more halogen atoms. The hydrocarbon having 2 or more carbon atoms and substituted with 5 or more halogen atoms is preferably a saturated hydrocarbon having 2 or more carbon atoms and substituted with 5 or more halogen atoms. The hydrocarbon having 2 or more carbon atoms and substituted with 5 or more halogen atoms includes, for example, pentachloroethane, pentafluoroethane, pentabromoethane, hexachloroethane, hexafluoroethane, 1,1,2,2,3-pentafluoropropane, 1,2,3,4,5,6-hexachlorocyclohexane, hexabromoethane, etc.

(Nitrogen-Containing Compound)

The catalyst for use in the present invention contains a transition metal-containing compound, an aluminium-containing compound and a hydrocarbon having 2 or more carbon atoms and substituted with a halogen atom as the constitutive components of the catalyst, and, in addition to these, preferably further contains a nitrogen-containing compound as the catalyst component.

In the present invention, the nitrogen-containing compound is a compound containing a nitrogen atom in the molecule, and includes, for example, amines, amides, imides, etc.

The amines include, for example, pyrrole compounds. Specific examples of the compounds include pyrroles, such as pyrrole, 2,4-dimethylpyrrole, 2,5-dimethylpyrrole, 2,5-diethylpyrrole, 2,4-diethylpyrrole, 2,5-di-n-propylpyrrole, 2,5-di-n-butylpyrrole, 2,5-di-n-pentylpyrrole, 2,5-di-n-hexylpyrrole, 2,5-dibenzylpyrrole, 2,5-diisopropylpyrrole, 2-methyl-5-ethylpyrrole, 2,5-dimethyl-3-ethylpyrrole, 3,4-dimethylpyrrole, 3,4-dichloropyrrole, 2,3,4,5-tetrachloropyrrole, 2-acetylpyrrole, indole, 2-methylindole, and dipyrrole where two pyrrole rings bond via a substituent, and derivatives thereof. The derivatives include, for example, metal pyrrolide derivatives, and specific examples thereof include, for example, aluminium pyrrolides such as diethylaluminium pyrrolide, ethylaluminium dipyrrolide, aluminium tripyrrolide, diethylaluminium (2,5-dimethylpyrrolide), ethylaluminium bis(2,5-dimethylpyrrolide), aluminium tris(2,5-dimethylpyrrolide), diethylaluminium (2,5-diethylpyrrolide), ethylaluminium bis(2,5-diethylpyrrolide), aluminium tris(2,5-diethylpyrrolide), etc.; sodium pyrrolides such as sodium pyrrolide, sodium (2,5-dimethylpyrrolide), etc.; lithium pyrrolides such as lithium pyrrolide, lithium (2,5-dimethylpyrrolide), etc.; potassium pyrrolides such as potassium pyrrolide, potassium (2,5-dimethylpyrrolide), etc. Aluminium pyrrolides are not within the category of the above-mentioned aluminium-containing compounds.

The amides include, for example, acetamide, N-methylhexanamide, succinamide, maleamide, N-methylbenzamide, imidazole-2-carboxamide, di-2-thenoylamine, β-lactam, 5-lactam, ε-caprolactam, and salts of these with a metal of Group 1, 2 or 13 of the Periodic Table.

The imides include, for example, 1,2-cyclohexanedicarboximide, succinimide, phthalimide, maleimide, 2,4,6-piperidinetrione, perhydroazecine-2,10-dione, and salts of these with a metal of Group 1, 2 or 13 of the Periodic Table. The sulfonamides and sulfonimides include, for example, benzenesulfonamide, N-methylmethanesulfonamide, N-methyltrifluoromethylsulfonamide, and salts of these with a metal of Group 1, 2 or 13 of the Periodic Table. One alone or two or more of these compounds may be used here either singly or as combined.

Among these, in the present invention, preferred are amines; and above all, more preferred are pyrrole compounds. Especially preferred is 2,5-dimethylpyrrole or diethylaluminium (2,5-dimethylpyrrolide).
(Catalyst Pre-Preparation)

The catalyst for use in the present invention contains a transition metal-containing compound, an aluminium-containing compound and a hydrocarbon having 2 or more carbon atoms and substituted with a halogen atom as the constitutive components of the catalyst, and preferably further contains a nitrogen-containing compound as the constitutive component. The usage pattern of the catalyst is not specifically limited. Preferably, the catalyst is brought into contact with the raw material, α-olefin in such a condition where the transition metal-containing compound and the aluminium-containing compound of the catalyst are not previously kept in contact with each other, or the pre-contact time for the two is short. The above-mentioned condition is preferred as favorably promoting the selective low polymerization reaction of the raw material α-olefin, therefore providing an α-olefin low polymer from the raw material at a high yield.

In the present invention, the "condition where the transition metal-containing compound and the aluminium-containing compound are not previously kept in contact with each other, or the pre-contact time for the two is short" means that the above-mentioned condition is kept not only at the start of the reaction but also during the period where the raw material, α-olefin and the catalyst components are additionally supplied in the reactor.

However, the above-mentioned specific condition is a preferred condition required in preparing the catalyst, and has no relation after the catalyst has been prepared. Accordingly, in case where the catalyst that has been already prepared is collected from the reaction system and reused in the system, the catalyst can be reused irrespective of the above-mentioned preferred condition.

In case where the catalyst comprises, for example, the above-mentioned four components, namely, the transition metal-containing compound (a), the nitrogen-containing compound (b), the aluminium-containing compound (c) and the hydrocarbon (d) having 2 or more carbon atoms and substituted with a halogen atom, the contact condition of those components generally includes the following:

(1) a method of introducing the catalyst component (a) into a solution containing the catalyst components (b), (c) and (d);

(2) a method of introducing the catalyst component (c) into a solution containing the catalyst components (a), (b) and (d);

(3) a method of introducing the catalyst components (b) and (c) into a solution containing the catalyst components (a) and (d);

(4) a method of introducing the catalyst components (a) and (b) into a solution containing the catalyst components (c) and (d);

(5) a method of introducing the catalyst components (c) and (d) into a solution containing the catalyst components (a) and (b);

(6) a method of introducing the catalyst components (a) and (d) into a solution containing the catalyst components (b) and (c);

(7) a method of introducing the catalyst components (a), (b) and (d) into a solution containing the catalyst component (c);

(8) a method of introducing the catalyst components (b) to (d) to a solution containing the catalyst component (a);

(9) a method of introducing a liquid prepared by introducing the catalyst component (a) into a solution containing the catalyst components (b) and (c), and a solution containing the catalyst component (d), simultaneously and independently into a reactor (in which, if desired, a solution containing the catalyst component (c) may be further introduced into the reactor);

(10) a method of introducing the individual catalyst components (a) to (d) simultaneously and independently into a reactor.

Each solution in the above may be prepared generally using the solvent to be used in the reaction.
[Olefin Having 2 or More Carbon Atoms and Substituted with a Halogen Atom (it May be Referred to as "One or More Halogen Atoms")]

The olefin having 2 or more carbon atoms and substituted with one or more halogen atom in the present invention is an olefinic hydrocarbon having a halogen atom bonding to the carbon atom of the double bond therein, and is preferably an unsaturated halogenohydrocarbon having a lowered halogen atom number relative to the above-mentioned hydrocarbon having 2 or more carbon atoms and substituted with a halogen atom. More preferred is a decomposed product of the hydrocarbon having 2 or more carbon atoms and substituted with a halogen atom. Even more preferred is a decomposed product of a hydrocarbon having 2 or more carbon atoms and substituted with 3 or more halogen atoms.

The production method for an α-olefin low polymer of the present invention (the first aspect of the invention) comprises, as described in detail hereinunder, a reaction step, a purification step and a circulation step of circulating the unreacted raw material α-olefin and the solvent from the purification step to the reaction step, in which, the unreacted raw material α-olefin to be supplied from the circulation step to the reaction step, the amount of the olefin having 2 or more carbon atoms and substituted with one or more halogen atoms must be within a range of from 0.1 to less than 200 (molar ratio) relative to the amount of the transition metal in the reaction step. This is described below.

In the present invention, the hydrocarbon having 2 or more carbon atoms and substituted with a halogen atom that is used as one catalyst component is almost entirely decomposed in the reaction step to give, as a side product, an olefin having 2 or more carbon atoms and substituted with one or more halogen atoms. This exists in the reaction mixture and is supplied to the purification step along with the intended product and the solvent therewith.

The purification step includes a step of separating the unreacted raw material α-olefin, a step of separating a high-boiling-point substance, and a step of separating the product. In case where the boiling point of the side product is close to that of the unreacted raw material α-olefin, the side product could be separated in the step of separating the unreacted raw material α-olefin and could be circulated in the reaction step along with the unreacted raw material α-olefin thereinto. On the other hand, when the boiling point of the side product is close to that of the solvent, the side product could be separated in the step of separating the product, and could be circulated to the reaction step along with the solvent thereinto. In case where the side product is converted into a high-boiling-point substance, the substance could be separated in the step of separating a high-boiling-point substance.

In the reaction step, the hydrocarbon having 2 or more carbon atoms and substituted with a halogen atom, which has been supplied in the initial stage, a compound (side product) formed by decomposing the hydrocarbon during the reaction, and the side product that has been supplied from the circulation step would exist as mixed therein.

Heretofore, it has been considered that an olefin having 2 or more carbon atoms and substituted with one or more halogen atoms would interfere with reaction, and therefore circulating the olefin discharged from the reaction step, again into the reaction step has been considered to be unfavorable since the olefin would accumulate in the reaction step. Surprisingly, however, in the present invention, it has found that the olefin promotes the catalyst reaction and improves the intended product selectivity.

Though not clear, the reason would be that the olefin having 2 or more carbon atoms and substituted with one or more halogen atoms could supply a halogen atom to the catalyst in the solvent, like the hydrocarbon having 2 or more carbon atoms and substituted with a halogen atom, so far as the amount thereof falls within a specific range, and, as a result, the selectivity of the intended product could be thereby improved.

According to the present invention, by bringing the amount of the olefin having 2 or more carbon atoms and substituted with one or more halogen atom that is supplied from the circulation step to the reaction step within the range of from 0.1 to less than 200 (molar ratio) relative to the amount of the transition metal in the reaction step, there can be provided a reaction system capable of improving the selectivity of the intended product.

The upper limit of the molar ratio is preferably 170, more preferably 120. The lower ratio of the molar ratio is preferably 0.5, more preferably 1.0, even more preferably 3.0, especially preferably 10.0. When the molar ratio falls within the above range, then it is possible to supply halogen atoms to the catalyst without interfering with the reaction.

In the present invention, in a case where the hydrocarbon having 2 or more carbon atoms and substituted with a halogen atom is 1,1,2,2-tetrachloroethane, the olefin having 2 or more carbon atoms and substituted with one or more halogen atoms is preferably 1,2-dichloroethylene; and in a case where the hydrocarbon having 2 or more carbon atoms and substituted with a halogen atom is a hydrocarbon having 2 or more carbon atoms and substituted with 5 or more halogen atoms, the olefin having 2 or more carbon atoms and substituted with one or more halogen atoms is preferably an olefin having 2 or more carbon atoms and substituted with 3 or more halogen atoms.

Here, in a case where the olefin having 2 or more carbon atoms and substituted with one or more halogen atoms is 1,2-dichloroethylene (this may be referred to as DCE), in particular, the lower limit of the amount thereof relative to the amount of the transition metal in the reaction step is preferably 0.1 or more and the upper limit thereof is preferably less than 100 (molar ratio), more preferably less than 85, even more preferably less than 55.

As a more preferred embodiment of the present invention, the supply amount to the reaction step of the hydrocarbon having 2 or more carbon atoms and substituted with a halogen atom is within a range of from 0.5 to 50 (molar ratio) relative to the supply amount to the reaction step of the transition metal, and the amount of the olefin having 2 or more carbon atoms and substituted with one or more halogen atoms that is supplied from the circulation step to the reaction step is 2 or more (molar ratio) relative to the amount of the hydrocarbon having 2 or more carbon atoms and substituted with a halogen atom, and is less than 200 (molar ratio) relative to the amount of the transition metal in the reaction step. The concentration of the olefin having 2 or more carbon atoms and substituted with one or more halogen atoms in the circulation solvent may be measured using a gas chromatography or the like analyzer.

The saturated hydrocarbon having 2 or more carbon atoms and substituted with a halogen atom gives the halogen atom to the transition metal to form a catalytic active species, but with the progress of reaction, there may be formed a degraded catalyst species with which the selectivity and the purity of the intended product may lower. According to the method of the present invention, an environment where a halogen atom can be smoothly imparted to the degraded catalyst species may be provided and the catalytic active species can be thereby formed.

The method of controlling the amount of the olefin having 2 or more carbon atoms and substituted with one or more halogen atom, which is supplied from the circulation step, to be the above-mentioned one is not specifically limited. Examples include a method in which, in the purification step, the reflux ratio may be controlled in the unreacted raw material α-olefin separation tower, and the circulation amount of the olefin having 2 or more carbon atoms and substituted with one or more halogen atoms can be thereby controlled.

The production method for an α-olefin low polymer of the present invention (the second aspect of the invention) is based on the finding of the above-mentioned first aspect of the invention, but the method is applicable to a batch process not requiring a circulation step. Specifically, the method is for producing an α-olefin low polymer through low polymerization reaction of an α-olefin in the presence of a catalyst containing a transition metal-containing compound, an aluminium-containing compound and a saturated hydrocarbon having 2 or more carbon atoms and substituted with a halogen atom, and a solvent, wherein an olefin having 2 or more carbon atoms and substituted with one or more halogen atoms is supplied in the reaction step within a range of from 0.1 to less than 200 (molar ratio) relative to the amount of the transition metal in the reaction step.

In this case, it is self-evident that the olefin having 2 or more carbon atoms and substituted with one or more halogen atoms that may exist in the reaction system through decomposition of the saturated hydrocarbon having 2 or more carbon atoms and substituted with a halogen atom in the reaction system is not within the category of the olefin having 2 or more carbon atoms and substituted with one or more halogen atoms that is supplied in the reaction step.

In addition, it is also self-evident that the effect of the second aspect of the present invention is the same as in the case where a specific amount of an olefin having 2 or more carbon atoms and substituted with one or more halogen atom that is derived from the circulation from the purification step in the first aspect of the invention, is made to exist in the reaction step.

The olefin having 2 or more carbon atoms and substituted with one or more halogen atoms includes, for example, 1,1-dichloroethylene, 1,2-dichloroethylene, trichloroethylene, tetrachloroethylene (perchloroethylene), trifluoroethylene, perfluoroethylene, trifluoropropylene, tetrachlorocyclohexene, 1,1-dibromoethylene, 1,2-dibromoethylene, tribromoethylene, perbromoethylene, etc.

[Solvent]

In the production method for an α-olefin low polymer of the present invention, an α-olefin may be oligomerized in a solvent. The solvent is not specifically limited but is preferably a saturated hydrocarbon. For example, preferred examples of the solvent include linear saturated hydrocarbons having from 1 to 20 carbon atoms or alicyclic saturated hydrocarbons having from 1 to 20 carbon atoms, such as butane, pentane, 3-methylpentane, n-hexane, n-heptane, 2-methylhexane, octane, cyclohexane, methylcyclohexane, 2,2,4-trimethylpentane, decalin, etc. In addition, aromatic hydrocarbons such as benzene, toluene, xylene, ethylbenzene, mesitylene, tetralin and the like are usable as the solvent for α-olefin low polymer. Further, 1-hexene, decene or the like formed through low polymerization reaction of an α-olefin is also usable as the reaction solvent. One alone or two more of these may be used here as a single solvent or a mixed solvent.

Of those solvents, preferred is use of linear saturated hydrocarbons or alicyclic saturated hydrocarbons having from 4 to 10 carbon atoms, from the viewpoint of preventing the formation or precipitation of side-product polymers such as polyethylene and the like, and further from the viewpoint of the ability to realize a high catalyst activity. Concretely, preferred is n-heptane or cyclohexane; and most preferred is n-heptane.

[α-Olefin]

The α-olefin to be used as the raw material in the method for producing an α-olefin low polymer of the present invention includes, for example, a substituted or unsubstituted α-olefin having from 2 to 30 carbon atoms. Specific examples of the α-olefin of the type include ethylene, propylene, 1-butene, 1-hexene, 1-octene, 3-methyl-1-butene, 4-methyl-1-pentene, etc. Among these, as the raw material α-olefin in the present invention, preferred is ethylene. In case where ethylene is used as the raw material, a trimer of ethylene which is 1-hexene, can be produced at a high yield and at a high selectivity.

In the case where ethylene is used as the raw material, the raw material may contain any other impurity component than ethylene. Specific examples of the component include methane, ethane, nitrogen, acetylene, carbon dioxide, carbon monoxide, oxygen, sulfur, water, etc. There would not be any specific limitation on methane, ethane and nitrogen, but preferably the content thereof is 0.1 mol % or less relative to the raw material ethylene. The content of the other impurities is preferably 1 molppm or less relative to the raw material ethylene.

[Low Polymerization Reaction of α-Olefin]

The ratio of the constitutive components of the catalyst for use in the present invention is not specifically limited, but may be generally as follows.

The amount of the hydrocarbon having 2 or more carbon atoms and substituted with a halogen atom is generally 0.5 mol or more relative to one mol of the transition metal-containing compound, preferably 1 mol or more, and is generally 50 mol or less, preferably 30 mol or less, even more preferably 10 mol or less.

The amount of the aluminium-containing compound is from 1 mol to 200 mol relative to one mol of the transition metal-containing compound, and preferably from 10 mol to 150 mol.

The nitrogen-containing compound, if any, in the catalyst is generally in an amount of from 1 mol to 50 mol, preferably from 1 mol to 30 mol, relative to 1 mol of the transition metal-containing compound.

In the present invention, the amount of the catalyst to be used is not specifically limited. In general, the transition metal atom-equivalent amount of the transition metal-containing compound per 1 liter of the solvent is from $1.0 \times 10^{-9}$ mol to 0.5 mol, preferably from $5.0 \times 10^{-9}$ mol to 0.2 mol, more preferably from $1.0 \times 10^{-8}$ mol to 0.05 mol.

Using the catalyst and, for example, using ethylene as the raw material gives a trimer of ethylene, hexane, at a selectivity of 90% or more. Further, in the case, the proportion of 1-hexene to hexene could be 99% or more.

The low polymerization reaction temperature for α-olefin is not specifically limited. In general, the temperature may be from 0 to 250° C., preferably from 50 to 200° C., even more preferably from 80 to 170° C.

The pressure of the raw material α-olefin during the reaction is not specifically limited. In general, the pressure may be from 0 to 25 MPa as the gauge pressure, preferably from 0.5 to 15 MPa, more preferably from 1.0 to 10 MPa.

In the present invention, the residence time in the reactor is not specifically defined. In general, the time is from 1 minute to 10 hours, preferably from 3 minutes to 3 hours, more preferably from 5 minutes to 40 minutes.

The reaction mode in the present invention is not specifically limited and it may be any of batch-type, semi-batch-type or continuous reaction. The actual equipment is preferably a continuous system in view of a comprehensive judgment including the purification step, but for realizing the advantageous effects of the present invention, the reaction mode may also be a batch-type one.

In a case of trimerization of ethylene, the molar ratio of 1-hexene to ethylene in the reaction liquid ((molar concentration of 1-hexene in the reaction liquid)/(molar concentration of ethylene in the reaction liquid)) is not specifically defined. In the case, preferably, the ratio is from 0.05 to 1.5, more preferably from 0.10 to 1.0. Specifically, in a case of continuous reaction, it is desirable that the catalyst concentration, the reaction pressure and other conditions are controlled so that the molar ratio of 1-hexene to ethylene in the reaction liquid could fall within the above-mentioned range. In a case of batch reaction, it is desirable that the trimerization of ethylene is stopped at a certain time when the molar ratio falls within the above-mentioned range. Trimerization of ethylene under the condition tends to further increase the selectivity of 1-hexene while preventing production of any side product having a higher boiling point than that of 1-hexene.

[α-Olefin Low Polymer]

The above reaction gives an α-olefin low polymer. In the present invention, the α-olefin low polymer means an oligomer in which a few molecules of the α-olefin as the monomer bond to each other. Concretely, the α-olefin low polymer is a polymer where from 2 to 10 molecules of the α-olefin as the monomer bond to each other. Preferably, the oligomer is 1-hexene formed through selective trimerization of ethylene.

[Production Method for α-Olefin Low Polymer]

The method for producing an α-olefin low polymer is described for an low polymerization reaction case where ethylene is used as the α-olefin to give a trimer of ethylene, 1-hexene, as the α-olefin low polymer, with reference to FIGURE. However, the method is not limited to the case.

FIGURE shows a reaction step of oligomerizing ethylene in the presence of a catalyst (a complete mixing and stirring-type reactor 10), and a purification step of purifying the reaction mixture discharged from the reactor 10 (hereinafter this may be referred to as "reaction liquid"). Concretely it shows a degassing tank 20 for separating unreacted ethylene gas, an ethylene separation tower 30 for distilling out ethylene from the reaction liquid discharged from the degassing tank 20, a high-boiling separation tower 40 for separating a high-boiling-point substance (hereinafter this may be referred to as "HB" (high boiler)) from the reaction liquid discharged from the ethylene separation tower 30, and a hexene separation tower 50 for distilling the reaction liquid distilled from the top of the high-boiling separation tower 40 to separate 1-hexene.

The unreacted ethylene separated in the degassing tank 20 is circulated to the reactor 10 via the circulation line 21 and the compressor 17. A newly-supplied ethylene material is continuously supplied to the reactor 10 from the ethylene supply line 12a via the compressor 17 and the first supply line 12.

The compressor 17 is, for example, in a case of a two-stage compression system, so planned that the circulation line 31 is connected in the first stage and the circulation line 21 is connected in the second stage to thereby reduce the power cost. From the second supply line 13, a solvent for use for ethylene low polymerization reaction may be supplied to the reactor 10.

The reactor 10 is not specifically limited. For example, the reactor may be any known one equipped with a stirrer 10a, a baffle, a jacket, etc. In the stirrer 10a, a stirring blade in the form of a paddle, a Pfaudler impeller, a propeller, a turbine or the like may be combined with a baffle in the form of a plate, a cylinder, a hair pin coil or the like.

On the other hand, a transition metal-containing compound and a nitrogen-containing compound that have been previously prepared in a catalyst tank are supplied to the reactor 10 through the second supply line 13 via the catalyst supply line 13a; an aluminium-containing compound is supplied through the third supply line 14; and a hydrocarbon having 2 or more carbon atoms and substituted with a halogen atom is supplied through the fourth supply line 15. Here, the saturated hydrocarbon having 2 or more carbon atoms and substituted with a halogen atom may be supplied to the reactor 10 through the second supply line 13 via the supply line. So far as the time for contact of the aluminium-containing compound and the transition metal-containing compound is within a few minutes and the two are supplied to the reactor 10 within the time, then the aluminium-containing compound may also be supplied to the reactor 10 through the second supply line 13 through the supply line. In the system of the case, a static mixer or the like may be installed between the second supply line 13 and the reactor 10 to reduce the stirring power for the reactor 10 since a uniform mixture of the catalyst components may be supplied to the reactor 10.

For the method for making an olefin having 2 or more carbon atoms and substituted with one or more halogen atoms exist in the reactor, the olefin may be supplied to the reactor along with the compounds to be the catalyst constitutive components through the catalyst supply line 13a, the third supply line 14, the fourth supply line 15, etc. The olefin having 2 or more carbon atoms and substituted with one or more halogen atoms that has been distilled out of the reactor is separated from the reaction liquid in the distillation tower existing after the reactor, along with the solvent therefrom. The solvent is discharged out from the hexene separation tower 50, and is circulated to the reaction step via the circulation step. Specifically, in circulating the solvent from the second supply line 13 to the reactor via the solvent circulation line 52 for reusing it, a part of the olefin having 2 or more carbon atoms and substituted with one or more halogen atoms may be supplied to the reactor, depending on the distillation condition in the distillation tower. Consequently, in continuous operation, for controlling the amount of the olefin having 2 or more carbon atoms and substituted with one or more halogen atoms existing in the reactor, the distillation condition in the high-boiling separation tower 40 and the hexene separation tower 50 may be controlled to thereby control the amount of the olefin.

The reaction mixture continuously discharged out from the reactor 10 via the line 11 is, after the ethylene trimerization is stopped by the deactivator supplied through the deactivator supply line 11a, supplied to the degassing tank 20.

The driving condition for the degassing tank 20 is not specifically defined. In general, the temperature is from 0 to 250° C., preferably from 50 to 200° C., and the pressure is from 0 to 15 MPa as the gauge pressure, preferably from 0 to 9 MPa. Accordingly, the unreacted ethylene is discharged out from the top of the degassing tank 20 and the reaction liquid from which the unreacted ethylene has been degassed is discharged out from the bottom of the tank.

The reaction liquid discharged out from the bottom of the degassing tank 20 is supplied to the ethylene separation tower 30 via the line 22. The driving condition for the ethylene separation tower 30 is not specifically limited. In general, the tower top pressure is from 0 to 3 MPa as the gauge pressure, preferably from 0 to 2 MPa. The reflux ratio (R/D) is not specifically defined, but is generally from 0 to 500, preferably from 0.1 to 100. Accordingly, ethylene is distilled out from the top of the ethylene separation tower 30, and the reaction liquid is discharged out from the bottom of the tower. The distilled ethylene is circulated to the reactor 10 via the circulation line 31 and the first supply line 12.

The bottom liquid discharged out from the ethylene separation tower 30 is supplied to the high-boiling separation tower 40 via the line 32. The driving condition for the high-boiling separation tower 40 is not specifically limited. In general, the tower top pressure is from 0 to 10 MPa as the gauge pressure, preferably from 0 to 0.5 MPa. The reflux ratio (R/D) is not specifically defined, but is generally from 0 to 100, preferably from 0.1 to 20. Accordingly, a high-boiling-point component (HB: high boiler) is discharged out from the tower bottom, and a distillate is discharged out from the tower top.

In the present invention, the circulation amount of the olefin having 2 or more carbon atoms and substituted with one or more halogen atoms to the reactor may be controlled by controlling the distillation condition in the high-boiling separation tower 40 and the hexene separation tower 50. Anyone skilled in the art can suitably determine the distillation condition in this case by monitoring the supply amount of the olefin having 2 or more carbon atoms and substituted with one or more halogen atoms to the reactor.

At the start of the production operation, the reaction is started in the state where the amount of the olefin having 2 or more carbon atoms and substituted with one or more halogen atoms in the circulation step falls within a range of from 0.1 to less than 200 (molar ratio) relative to the amount of the transition metal in the reaction step, whereby the amount of the olefin having 2 or more carbon atoms and substituted with one or more halogen atoms may be made to fall within the range during the production operation. Accordingly, there can be provided an environment where a halogen atom can be rapidly supplied to the transition metal from the start of the production operation, and a catalyst active species can be formed and the selectivity and the purity of the intended product can be thereby improved.

The distillate from the high-boiling separation tower 40 is supplied to the hexene separation tower 50 via the line 41. The driving condition for the hexene separation tower 50 is not specifically limited. In general, the tower top pressure is from 0 to 10 MPa as the gauge pressure, preferably from 0 to 0.5 MPa. The reflux ratio (RID) is generally from 0 to 100, preferably from 0.1 to 20. Accordingly, 1-hexene is discharged out from the tower top, and the solvent (for example, heptane) is discharged out from the tower bottom, and the solvent is circulated and supplied to the reactor 10 as a reaction solvent therein via the solvent circulation line 52 and the second supply line 13. In this stage, the nitrogen-containing compound of one catalyst component in the heptane solvent that is continuously circulated and supplied to the reactor 10, as discharged out from the bottom of the hexene separation tower 50, may also be continuously circulated and supplied to the reactor 10, like the heptane solvent thereinto. The concentration of the nitrogen-containing compound in the solvent circulated and supplied in a static state is not specifically defined, but is preferably 5.0 wtppm or more.

EXAMPLES

The present invention is described further concretely with reference to Examples. Not overstepping the scope and the spirit thereof, the invention is not limited to the following Examples.

Examples 1, 2, 3 and Comparative Example 1

Examples 1, 2 and 3 relative to Comparative Example 1 demonstrate the effect of trans-1,2-dichloroethylene as a halogen source for catalyst like 1,1,2,2-tetrachloroethane.

Examples 4 to 8 and Comparative Example 1

Examples 4 to 8 relative to Comparative Example 1 demonstrate the effect of an olefin having 2 or more carbon atoms and substituted with a halogen atom, as a halogen source for catalyst like a hydrocarbon having 2 or more carbon atoms and substituted with 5 or more halogen atoms.
(Preparation of Catalyst Liquid)

In a nitrogen atmosphere, 0.37 g (3.9 mmol) of 2,5-dimethylpyrrole and 234 ml of n-heptane were put into a 500-ml, three-neck glass flask equipped with a stirrer, which had been dried by heating at 140° C. for 2 hours or more, and 8.91 ml (3.9 mmol) of triethylaluminium diluted with n-heptane to be 50 g/L was added thereto. Subsequently, the flask was immersed in an oil bath and heated, and n-heptane therein was refluxed at 98° C. in a nitrogen atmosphere for 3 hours to thereby prepare a nitrogen-containing compound, aluminium pyrrolide. Then, this was cooled to 80° C. Subsequently, 6.26 ml (0.65 mmol) of chromium(III) 2-ethylhexanoate diluted with n-heptane to be 50 g/L was added thereto. After the addition, this was heated and stirred at 80° C. for 30 minutes in a nitrogen atmosphere to prepare a catalyst liquid. Subsequently, the catalyst liquid was diluted with n-heptane so that the concentration of chromium(III) 2-ethylhexanoate therein could be 0.88 g/L.

Comparative Example 1

(Production of Hexene)

Next, a 500-ml autoclave kit that had been dried by heating at 140° C. for 2 hours or more was assembled while hot, and then purged with nitrogen in vacuum. A catalyst feed tube equipped with a pressure-resistant rupture disk was attached to the autoclave. 2 ml of the catalyst liquid prepared previously in the manner as above was fed into the feed tube. Into the body of the autoclave, supplied were 165 ml of a reaction solvent, n-heptane, 3 ml (0.20 mmol) of triethylaluminium diluted with n-heptane to be 7.67 g/L, and 5 ml of n-undecane for use as an internal standard in compositional analysis through gas chromatography.

The autoclave was heated up to 140° C., ethylene was introduced thereinto through the catalyst feed tube, and ethylene low polymerization reaction was started. During the reaction, the temperature in the autoclave was kept at 140° C. and the total pressure therein was at 7 MPaG.

After 60 minutes, ethylene introduction with stirring was stopped, then the autoclave was rapidly cooled and thereafter the whole amount of the gas was sampled through the vapor phase nozzle. Then, the reaction liquid was sampled, and each was subjected to compositional analysis through gas chromatography. In addition, the reaction liquid was filtered and dried, and the weight of the polymer contained in the reaction liquid was measured. The catalyst activity was calculated by dividing the weight of the reaction product (unit: g) obtained through the reaction for 60 minutes by the atomic weight of the transition metal (unit: g) in the transition metal catalyst component used in the reaction.

The molar ratio of the catalyst components, the molar ratio of 1,2-dichloroethylene relative to the amount of the transition metal in the reaction step (in Table 1, molar ratio of DCE to (a)), and the results are shown in Table 1.

Example 1

The production was carried out in the same manner as Comparative Example 1, except that 163 ml of n-heptane and 1.8 ml (0.018 mmol) of trans-1,2-dichloroethylene diluted with n-heptane to be 1.0 g/L were supplied to the body of the autoclave. The molar ratio of the catalyst components, the molar ratio of 1,2-dichloroethylene relative to the amount of the transition metal in the reaction step (in Table 1, molar ratio of DCE to (a)), and the results are shown in Table 1.

Example 2

The production was carried out in the same manner as Comparative Example 1, except that 161 ml of n-heptane and 3.6 ml (0.037 mmol) of trans-1,2-dichloroethylene diluted with n-heptane to be 1.0 g/L were supplied to the body of the autoclave. The molar ratio of the catalyst components, the molar ratio of 1,2-dichloroethylene relative to the amount of the transition metal in the reaction step (in Table 1, molar ratio of DCE to (a)), and the results are shown in Table 1.

Example 3

The production was carried out in the same manner as Comparative Example 1, except that 158 ml of n-heptane and 7.2 ml (0.074 mmol) of trans-1,2-dichloroethylene diluted with n-heptane to be 1.0 g/L were supplied to the body of the autoclave. The molar ratio of the catalyst components, the molar ratio of 1,2-dichloroethylene relative to the amount of the transition metal in the reaction step (in Table 1, molar ratio of DCE to (a)), and the results are shown in Table 1.

TABLE 1

| | Ratio of Catalyst Components (molar ratio) (a)/(b)/(c)/(d) | Molar Ratio of DCE to (a) | Catalyst Activity [g/g-Cr] | C6 Component in Product [wt %] | 1-Hexene Contained in C6 [wt %] |
|---|---|---|---|---|---|
| Example 1 | 1/6/60/0 | 5 | 286000 | 77.0 | 95.6 |
| Example 2 | 1/6/60/0 | 10 | 345000 | 81.7 | 96.8 |
| Example 3 | 1/6/60/0 | 20 | 339000 | 86.8 | 97.7 |
| Comparative Example 1 | 1/6/60/0 | 0 | 119000 | 57.3 | 90.5 |

(a) Chromium(III) 2-ethylhexanoate
(b) 2,5-Dimethylpyrrole
(c) Triethylaluminium
(d) 1,1,2,2-Tetrachloroethane
DCE Trans-1,2-dichloroethylene
C6 Aliphatic hydrocarbon having 6 carbon atoms The results in Table 1 verify that the reaction system with 1,2-dichloroethylene (DCE) existing therein (Examples 1, 2, 3) provides extremely excellent results in point of the catalyst activity, the content of the intended product (C6 component) in the product and the content of the intended product (1-hexene) in C6, as compared with the reaction system where no chlorine source exists (Comparative Example 1). These indicate that DCE, which is a decomposition product of 1,1,2,2-tetrachloroethane and which has heretofore been considered to interfere with reaction, acts as a catalyst promoter capable of supplying a chlorine atom of a halogen atom to the chromium catalyst of a transition metal.

Example 4

The production was carried out in the same manner as Comparative Example 1, except that 164 ml of n-heptane and 1.2 ml (0.0036 mmol) of perchloroethylene diluted with n-heptane to be 0.5 g/L were supplied to the body of the autoclave. The molar ratio of the catalyst components, the molar ratio of perchloroethylene relative to the amount of the transition metal in the reaction step (in Table 2, molar ratio of PCE to (a)), and the results are shown in Table 2.

Example 5

The production was carried out in the same manner as Comparative Example 1, except that 159 ml of n-heptane and 6 ml (0.018 mmol) of perchloroethylene diluted with n-heptane to be 0.5 g/L were supplied to the body of the autoclave. The molar ratio of the catalyst components, the molar ratio of perchloroethylene relative to the amount of the transition metal in the reaction step (in Table 2, molar ratio of PCE to (a)), and the results are shown in Table 2.

Example 6

The production was carried out in the same manner as Comparative Example 1, except that 163 ml of n-heptane and 1.5 ml (0.090 mmol) of perchloroethylene diluted with n-heptane to be 10 g/L were supplied to the body of the autoclave. The molar ratio of the catalyst components, the molar ratio of perchloroethylene relative to the amount of the transition metal in the reaction step (in Table 2, molar ratio of PCE to (a)), and the results are shown in Table 2.

Example 7

The production was carried out in the same manner as Comparative Example 1, except that 162 ml of n-heptane and 3 ml (0.18 mmol) of perchloroethylene diluted with n-heptane to be 10 g/L were supplied to the body of the autoclave. The molar ratio of the catalyst components, the molar ratio of perchloroethylene relative to the amount of the transition metal in the reaction step (in Table 2, molar ratio of PCE to (a)), and the results are shown in Table 2.

Example 8

The production was carried out in the same manner as Comparative Example 1, except that 159 ml of n-heptane and 6 ml (0.36 mmol) of perchloroethylene diluted with n-heptane to be 10 g/L were supplied to the body of the autoclave. The molar ratio of the catalyst components, the molar ratio of perchloroethylene relative to the amount of the transition metal in the reaction step (in Table 2, molar ratio of PCE to (a)), and the results are shown in Table 2.

TABLE 2

| | Ratio of Catalyst Components (molar ratio) (a)/(b)/(c)/(d) | Molar Ratio of PCE to (a) | Catalyst Activity [g/g-Cr] | C6 Component in Product [wt %] | 1-Hexene Contained in C6 [wt %] |
|---|---|---|---|---|---|
| Example 4 | 1/6/60/0 | 1 | 218000 | 71.5 | 93.8 |
| Example 5 | 1/6/60/0 | 5 | 305000 | 77.9 | 95.7 |
| Example 6 | 1/6/60/0 | 25 | 397000 | 89.8 | 98.0 |
| Example 7 | 1/6/60/0 | 50 | 367000 | 92.7 | 98.7 |
| Example 8 | 1/6/60/0 | 100 | 247000 | 95.2 | 99.0 |
| Comparative Example 1 | 1/6/60/0 | 0 | 119000 | 57.3 | 90.5 |

(a) Chromium(III) 2-ethylhexanoate
(b) 2,5-Dimethylpyrrole
(c) Triethylaluminium
(d) Hexachloroethane
PCE Perchloroethylene
C6 Aliphatic hydrocarbon having 6 carbon atoms The results in Table 2 verify that the reaction system with perchloroethylene (PCE) existing therein (Examples 4 to 8) provides extremely excellent results in point of the catalyst activity, the content of the intended product (C6 component) in the product and the content of the intended product (1-hexene) in C6, as compared with the reaction system where no chlorine source exists (Comparative Example 1). These show that PCE, which is a decomposition product of hexachloroethane and which has heretofore been considered to interfere with reaction, acts as a catalyst promoter capable of supplying a chlorine atom of a halogen atom to the chromium catalyst of a transition metal.

Comparative Example 2

The production was carried out in the same manner as Comparative Example 1, except that 164 ml of n-heptane and 0.6 ml (0.0018 mmol) of 1,1,2,2-tetrachloroethane diluted with n-heptane to be 0.5 g/L were supplied to the body of the autoclave. The molar ratio of the catalyst components, the molar ratio of 1,2-dichloroethylene relative to the amount of the transition metal in the reaction step (in Table 3, molar ratio of DCE to (a)), and the results are shown in Table 3.

Example 9

The production was carried out in the same manner as Comparative Example 2, except that 163 ml of n-heptane and 0.7 ml (0.0036 mmol) of trans-1,2-dichloroethylene diluted with n-heptane to be 0.5 g/L were supplied to the body of the autoclave. The molar ratio of the catalyst components, the molar ratio of 1,2-dichloroethylene relative to the amount of the transition metal in the reaction step (in Table 3, molar ratio of DCE to (a)), and the results are shown in Table 3.

TABLE 3

| | Ratio of Catalyst Components (molar ratio) (a)/(b)/(c)/(d) | Molar Ratio of DCE to (a) | Catalyst Activity [g/g-Cr] | C6 Component in Product [wt %] | 1-Hexene Contained in C6 [wt %] |
|---|---|---|---|---|---|
| Example 9 | 1/6/60/0.5 | 1 | 323000 | 76.1 | 95.6 |
| Comparative Example 2 | 1/6/60/0.5 | 0 | 281000 | 74.2 | 94.7 |

(a) Chromium(III) 2-ethylhexanoate
(b) 2,5-Dimethylpyrrole
(c) Triethylaluminium
(d) 1,1,2,2-Tetrachloroethane
DCE Trans-1,2-dichloroethylene
C6 Aliphatic hydrocarbon having 6 carbon atoms The results in Table 3 verify that Example 9 shows improvement in the catalyst activity, increase in the content of the C6 component in the product and increase in the 1-hexene content contained in C6, as compared with Comparative Example 2 where the initial supply of 1,2-dichloroethylene(DCE) in the reactor is 0.

Comparative Example 3

The production was carried out in the same manner as Comparative Example 1, except that 164 ml of n-heptane and 0.86 ml (0.0018 mmol) of hexachloroethane diluted with n-heptane to be 0.5 g/L were supplied to the body of the autoclave. The molar ratio of the catalyst components, the molar ratio of perchloroethylene relative to the amount of the transition metal in the reaction step (in Table 4, molar ratio of PCE to (a)), and the results are shown in Table 4.

Example 10

The production was carried out in the same manner as Comparative Example 3, except that 163 ml of n-heptane and 1.2 ml (0.0036 mmol) of hexachloroethane diluted with n-heptane to be 0.5 g/L were supplied to the body of the autoclave. The molar ratio of the catalyst components, the molar ratio of perchloroethylene relative to the amount of the transition metal in the reaction step (in Table 4, molar ratio of PCE to (a)), and the results are shown in Table 4.

Example 11

The production was carried out in the same manner as Comparative Example 3, except that 158 ml of n-heptane and 6 ml (0.36 mmol) of perchloroethylene diluted with n-heptane to be 10 g/L were supplied to the body of the autoclave. The molar ratio of the catalyst components, the molar ratio of perchloroethylene relative to the amount of the transition metal in the reaction step (in Table 4, molar ratio of PCE to (a)), and the results are shown in Table 4.

TABLE 4

| | Ratio of Catalyst Components (molar ratio) (a)/(b)/(c)/(d) | Molar Ratio of PCE to (a) | Catalyst Activity [g/g-Cr] | C6 Component in Product [wt %] | 1-Hexene Contained in C6 [wt %] |
|---|---|---|---|---|---|
| Example 10 | 1/6/60/0.5 | 1 | 287000 | 77.2 | 95.3 |
| Example 11 | 1/6/60/0.5 | 100 | 316000 | 94.6 | 99.0 |

TABLE 4-continued

| | Ratio of Catalyst Components (molar ratio) (a)/(b)/(c)/(d) | Molar Ratio of PCE to (a) | Catalyst Activity [g/g-Cr] | C6 Component in Product [wt %] | 1-Hexene Contained in C6 [wt %] |
|---|---|---|---|---|---|
| Comparative Example 3 | 1/6/60/0.5 | 0 | 281000 | 72.7 | 94.5 |

(a) Chromium(III) 2-ethylhexanoate
(b) 2,5-Dimethylpyrrole
(c) Triethylaluminium
(d) Hexachloroethane
PCE Perchloroethylene
C6 Aliphatic hydrocarbon having 6 carbon atoms The results in Table 4 verify that Examples 10 and 11 show improvement in the catalyst activity, increase in the content of the C6 component in the product and increase in the 1-hexene content contained in C6, as compared with Comparative Example 3 where the initial supply of perchloroethylene (PCE) in the reactor is 0.

Example 12

(Preparation of Catalyst)
The preparation is carried out in the same manner as Comparative Example 1.
(Production of Hexene)
Next, a 500-ml autoclave kit that had been dried by heating at 140° C. for 2 hours or more was assembled while hot, and then purged with nitrogen in vacuum. A catalyst feed tube equipped with a pressure-resistant rupture disk was attached to the autoclave. 2 ml of the catalyst liquid prepared previously in the manner as above was fed into the feed tube. Into the body of the autoclave, supplied were 162 ml of a reaction solvent, n-heptane, 3 ml (0.20 mmol) of triethylaluminium diluted with n-heptane to be 7.67 g/L, 1.7 ml (0.022 mmol) of 1,1,2,2-tetrachloroethane diluted with n-heptane to be 2.12 g/L, 1.4 ml (0.072 mmol) of trans-1,2-dichloroethylene diluted with n-heptane to be 5 g/L, and 5 ml of n-undecane for use as an internal standard in compositional analysis through gas chromatography.

The autoclave was heated up to 120° C., ethylene was introduced thereinto through the catalyst feed tube, and ethylene low polymerization reaction was started. During the reaction, the temperature in the autoclave was kept at 120° C. and the total pressure therein was at 6 MPaG.

After 30 minutes, ethylene introduction with stirring was stopped, then the autoclave was rapidly cooled and thereafter the whole amount of the gas was sampled through the vapor phase nozzle. Then, the reaction liquid was sampled, and each was subjected to compositional analysis through gas chromatography. In addition, the reaction liquid was filtered and dried, and the weight of the polymer contained in the reaction liquid was measured. The catalyst activity was calculated by dividing the weight of the reaction product (unit: g) obtained through the reaction for 30 minutes by the atomic weight of the transition metal (unit: g) in the transition metal catalyst component used in the reaction. The molar ratio of the catalyst components, the molar ratio of 1,2-dichloroethylene relative to the amount of the transition metal in the reaction step (in Table 5, molar ratio of DCE to (a)), and the results are shown in Table 5.

Example 13

The production was carried out in the same manner as Example 12, except that 160 ml of n-heptane and 3.5 ml (0.18 mmol) of trans-1,2-dichloroethylene diluted with n-heptane to be 5 g/L were supplied to the body of the autoclave. The results are shown in Table 5.

Example 14

The production was carried out in the same manner as Example 12, except that 158 ml of n-heptane and 5.7 ml (0.29 mmol) of trans-1,2-dichloroethylene diluted with n-heptane to be 5 g/L were supplied to the body of the autoclave. The results are shown in Table 5.

Example 15

The production was carried out in the same manner as Example 12, except that 156 ml of n-heptane and 7.1 ml (0.37 mmol) of trans-1,2-dichloroethylene diluted with n-heptane to be 5 g/L were supplied to the body of the autoclave. The results are shown in Table 5.

Example 16

The production was carried out in the same manner as Example 12, except that 158 ml of n-heptane and 5.3 ml (0.55 mmol) of trans-1,2-dichloroethylene diluted with n-heptane to be 10 g/L were supplied to the body of the autoclave. The results are shown in Table 5.

Comparative Example 4

The production was carried out in the same manner as Example 12, except that 163 ml of n-heptane was supplied to the body of the autoclave but a heptane solution of trans-1,2-dichloroethylene was not supplied thereto. The results are shown in Table 5.

Comparative Example 5

The production was carried out in the same manner as Example 12, except that 156 ml of n-heptane and 7.1 ml (0.73 mmol) of trans-1,2-dichloroethylene diluted with n-heptane to be 10 g/L were supplied to the body of the autoclave. The results are shown in Table 5.

TABLE 5

| | Ratio of Catalyst Components (molar ratio) (a)/(b)/(c)/(d) | Molar Ratio of DCE to (a) | Catalyst Activity [g/g-Cr] | C6 Component in Product [wt %] | 1-Hexene Contained in C6 [wt %] |
|---|---|---|---|---|---|
| Example 12 | 1/6/60/6 | 20 | 401000 | 94.2 | 98.9 |
| Example 13 | 1/6/60/6 | 50 | 336000 | 95.1 | 99.0 |
| Example 14 | 1/6/60/6 | 80 | 298000 | 95.3 | 99.1 |
| Example 15 | 1/6/60/6 | 100 | 268000 | 95.4 | 99.0 |
| Example 16 | 1/6/60/6 | 150 | 205000 | 95.9 | 99.2 |
| Comparative Example 4 | 1/6/60/6 | 0 | 373000 | 93.7 | 98.7 |
| Comparative Example 5 | 1/6/60/6 | 200 | 157000 | 96.8 | 99.3 |

(a) Chromium(III) 2-ethylhexanoate
(b) 2,5-Dimethylpyrrole
(c) Triethylaluminium
(d) 1,1,2,2-Tetrachloroethane
DCE Trans-1,2-dichloroethylene
C6 Aliphatic hydrocarbon having 6 carbon atoms The results in Table 5 verify that Examples 12 to 16 show increase in the content of the C6 component in the product and increase in the 1-hexene content contained in C6 while the catalyst activity is kept falling within an acceptable range, as compared with Comparative Example 4 where the initial supply of 1,2-dichloroethylene (DCE) in the reactor is 0. However, when the initial supply of DCE to the reactor is increased to be up to 200 mol relative to the chromium catalyst (Comparative Example 5), it is known that the catalyst activity greatly lowers.

Example 17

This is the same as in Example 12, except that 157 ml of n-heptane, 4.5 ml (0.057 mmol) of 1,1,2,2-tetrachloroethane diluted with n-heptane to be 2.12 g/L, and 3.6 ml (0.18 mmol) of trans-1,2-dichloroethylene diluted with n-heptane to be 5 g/L were supplied to the body of the autoclave. The results are shown in Table 6.

Example 18

The production was carried out in the same manner as Example 17, except that 153 ml of n-heptane, 4.5 ml (0.057 mmol) of 1,1,2,2-tetrachloroethane diluted with n-heptane to be 2.12 g/L, and 7.1 ml (0.37 mmol) of trans-1,2-dichloroethylene diluted with n-heptane to be 5 g/L were supplied to the body of the autoclave. The results are shown in Table 6.

Comparative Example 6

The production was carried out in the same manner as Example 17, except that 161 ml of n-heptane was supplied to the body of the autoclave but a heptane solution of trans-1,2-dichloroethylene was not supplied thereto. The results are shown in Table 6.

TABLE 6

| | Ratio of Catalyst Components (molar ratio) (a)/(b)/(c)/(d) | Molar Ratio of DCE to (a) | Catalyst Activity [g/g-Cr] | C6 Component in Product [wt %] | 1-Hexene Contained in C6 [wt %] |
|---|---|---|---|---|---|
| Example 17 | 1/6/60/16 | 50 | 296000 | 96.4 | 99.3 |
| Example 18 | 1/6/60/16 | 100 | 260000 | 96.4 | 99.2 |
| Comparative Example 6 | 1/6/60/16 | 0 | 442000 | 95.2 | 99.2 |

(a) Chromium(III) 2-ethylhexanoate
(b) 2,5-Dimethylpyrrole
(c) Triethylaluminium
(d) 1,1,2,2-Tetrachloroethylene
DCE Trans-1,2-dichloroethane
C6 Aliphatic hydrocarbon having 6 carbon atoms The results in Table 6 verify that Examples 17 and 18 show increase in the content of the C6 component in the product while the catalyst activity is kept falling within an acceptable range, as compared with Comparative Example 6 where the initial supply of 1,2-dichloroethylene (DCE) in the reactor is 0.

Example 19

(Preparation of Catalyst)
The preparation is carried out in the same manner as Comparative Example 1.
(Production of Hexene)
Next, a 500-ml autoclave kit that had been dried by heating at 140° C. for 2 hours or more was assembled while hot, and then purged with nitrogen in vacuum. A catalyst feed tube equipped with a pressure-resistant rupture disk was attached to the autoclave. 2 ml of the catalyst liquid prepared previously in the manner as above was fed into the feed tube. Into the body of the autoclave, supplied were 162 ml of a reaction solvent, n-heptane, 3 ml (0.20 mmol) of triethylaluminium diluted with n-heptane to be 7.67 g/L, 2.1 ml (0.022 mmol) of hexachloroethane diluted with n-heptane to be 2.46 g/L, 1.2 ml (0.072 mmol) of perchloroethylene diluted with n-heptane to be 10 g/L, and 5 ml of n-undecane for use as an internal standard in compositional analysis through gas chromatography.

The autoclave was heated up to 140° C., ethylene was introduced thereinto through the catalyst feed tube, and ethylene low polymerization reaction was started. During the reaction, the temperature in the autoclave was kept at 140° C. and the total pressure therein was at 7 MPaG.

After 60 minutes, ethylene introduction with stirring was stopped, then the autoclave was rapidly cooled and thereafter the whole amount of the gas was sampled through the vapor phase nozzle. Then, the reaction liquid was sampled, and each was subjected to compositional analysis through gas chromatography. In addition, the reaction liquid was filtered and dried, and the weight of the polymer contained in the reaction liquid was measured. The catalyst activity was calculated by dividing the weight of the reaction product (unit: g) obtained through the reaction for 60 minutes by the atomic weight of the transition metal (unit: g) in the transition metal catalyst component used in the reaction. The molar ratio of the catalyst components, the molar ratio of perchloroethylene relative to the amount of the transition metal in the reaction step (in Table 7, molar ratio of PCE to (a)), and the results are shown in Table 7.

Example 20

The production was carried out in the same manner as Example 19, except that 160 ml of n-heptane and 3.0 ml (0.18 mmol) of perchloroethylene diluted with n-heptane to be 10 g/L were supplied to the body of the autoclave. The results are shown in Table 7.

Example 21

The production was carried out in the same manner as Example 19, except that 157 ml of n-heptane and 6.0 ml (0.36 mmol) of perchloroethylene diluted with n-heptane to be 10 g/L were supplied to the body of the autoclave. The results are shown in Table 7.

Example 22

The production was carried out in the same manner as Example 19, except that 154 ml of n-heptane and 9.0 ml (0.54 mmol) of perchloroethylene diluted with n-heptane to be 10 g/L were supplied to the body of the autoclave. The results are shown in Table 7.

Comparative Example 7

The production was carried out in the same manner as Example 19, except that 163 ml of n-heptane was supplied to the body of the autoclave but a heptane solution of perchloroethylene was not supplied thereto. The results are shown in Table 7.

Comparative Example 8

The production was carried out in the same manner as Example 19, except that 151 ml of n-heptane and 12.0 ml (0.72 mmol) of perchloroethylene diluted with n-heptane to be 10 g/L were supplied to the body of the autoclave. The results are shown in Table 7.

TABLE 7

| | Ratio of Catalyst Components (molar ratio) (a)/(b)/(c)/(d) | Molar Ratio of PCE to (a) | Catalyst Activity [g/g-Cr] | C6 Component in Product [wt %] | 1-Hexene Contained in C6 [wt %] |
|---|---|---|---|---|---|
| Example 19 | 1/6/60/6 | 20 | 324000 | 93.5 | 98.9 |
| Example 20 | 1/6/60/6 | 50 | 295000 | 94.7 | 99.2 |
| Example 21 | 1/6/60/6 | 100 | 241000 | 95.0 | 99.9 |
| Example 22 | 1/6/60/6 | 150 | 196000 | 96.8 | 99.4 |
| Comparative Example 7 | 1/6/60/6 | 0 | 297000 | 92.2 | 98.8 |
| Comparative Example 8 | 1/6/60/6 | 200 | 127000 | 95.9 | 99.4 |

(a) Chromium(III) 2-ethylhexanoate
(b) 2,5-Dimethylpyrrole
(c) Triethylaluminium
(d) Hexachloroethane
PCE Perchloroethylene
C6 Aliphatic hydrocarbon having 6 carbon atoms Example 23

According to the production flow shown in FIGURE and using ethylene as the raw material α-olefin therein, 1-hexene was produced through continuous low polymerization reaction of ethylene. The production flow of FIGURE comprises a complete mixing and stirring-type reactor 10 for low polymerization reaction of ethylene in an n-heptane solvent and in the presence of a catalyst, a degassing tank 20 for separating unreacted ethylene gas from the reaction liquid discharged from the reactor 10, an ethylene separation tower 30 for distilling out ethylene from the reaction liquid discharged from the degassing tank 20, a high-boiling separation tower 40 for separating a high-boiling-point substance from the reaction liquid discharged from the ethylene separation tower 30, and a hexene separation tower 50 for distilling the reaction liquid distilled out from the top of the high-boiling separation tower 40 to separate 1-hexene. The n-heptane solvent separated in the hexene separation tower 50 is circulated to the reactor 10 via the solvent circulation line 52 and the second supply line 13. Further, the unreacted ethylene separated in the degassing tank 20 is circulated to the reactor 10 via the circulation line 21 and the compressor 17.

First, a solution of each catalyst component was supplied from a nitrogen-sealed tank (not shown) at 0.1 MPaG. Through the catalyst supply tube 13a, chromium(III)-2-ethylhexanoate (a) and 2,5-dimethylpyrrole (b) in an amount of 3.0 equivalents relative to the chromium(III)-2-ethylhexanoate (a) were continuously supplied to the reactor 10 via the second supply line 13. Triethylaluminium (c) was continuously supplied to the reactor 10 via the third supply line 14. Further, hexachloroethane (d) was continuously supplied to the reactor 10 via the fourth supply line 15. Regarding the reaction condition, the internal reactor temperature was 140° C. and the internal reactor pressure was 7.0 MPaG.

To the reaction liquid continuously discharged from the reactor 10, added was a catalyst deactivator, 2-ethylhexanol via the deactivator supply line 11a, and subsequently, this was processed in the degassing tank 20, the ethylene separation tower 30, the high-boiling separation tower 40 and the hexene separation tower 50 in that order.

The recovered n-heptane solvent separated in the hexene separation tower 50 was continuously supplied to the reactor 10 via the second supply line 13. In this stage, the reflux ratio in the high-boiling separation tower 40 was 0.6. All of 2.5-dimethylpyrrole (b) was not separated in the high-boiling separation tower but a part thereof was again fed to the reactor as recycled along with the recovered n-heptane solvent. In this stage, the concentration of 2.5-dimethylpyrrole (b) in the recovered n-heptane solvent was about 10 wtppm.

The ratio (molar ratio) of the catalyst components of the above (a) to (d) in the reactor 10 in a steady state was (a)/(b)/(c)/(d)=1/20/80/5, and the molar ratio of perchloroethylene in the circulating n-heptane solvent relative to chromium(III)-2-ethylhexanoate was 14. Perchloroethylene existed in the reactor as a side product resulting from decomposition of the halogen-containing compound.

The C6 selectivity was calculated by compositional analysis through gas chromatography (Shimadzu's GC-17AAF) of the circulating n-heptane solvent and the bottom residue from the ethylene separation tower 30, and the selectivity of each component formed in the reactor was thus calculated. The catalyst activity indicates the weight of the product (unit: g) formed in one hour per the chromium atom weight (unit: g) of the catalyst component supplied in 1 hour. The molar ratio of perchloroethylene to chromium(III)-2-ethylhexanoate (a) was calculated as follows. The perchloroethylene concentration in the circulating n-heptane solvent is measured through gas chromatography (Shimadzu's GC), then the perchloroethylene amount is calculated from the circulating n-heptane solvent amount, and this is divided by the amount of chromium(III)-2-ethylhexanoate (a) supplied to the reactor. The results are shown in Table 8.

Example 24

The production was carried out in the same manner as Example 23, except that the molar ratio of perchloroethylene relative to chromium(III)-2-ethylhexanoate (a) was 20. The results are shown in Table 8.

Example 25

The production was carried out in the same manner a Example 23, except that the molar ratio of perchloroethylene relative to chromium(III)2-ethylhexanoate (a) was 53. The results are shown in Table 8.

Example 26

The production was carried out in the same manner as Example 23, except that the molar ratio of the catalyst components in the reactor 10, (a)/(b)/(c)/(d)=1/20/80/4, and the molar ratio of perchloroethylene relative to chromium (III)-2-ethylhexanoate (a) was 67. The results are shown in Table 8.

TABLE 8

|  | Ratio of Catalyst Components (molar ratio) (a)/(b)/(c)/(d) | Molar Ratio of PCE to (a) | Catalyst Activity [g/g-Cr] | C6 Component in Product [wt %] | 1-Hexene Contained in C6 [wt %] |
|---|---|---|---|---|---|
| Example 23 | 1/20/80/5 | 14 | 970000 | 94.6 | 99.0 |
| Example 24 | 1/20/80/5 | 20 | 1010000 | 95.2 | 99.2 |
| Example 25 | 1/20/80/5 | 53 | 860000 | 96.1 | 99.4 |
| Example 26 | 1/20/80/4 | 67 | 880000 | 95.3 | 99.3 |

(a) Chromium(III)-2-ethylhexanoate
(b) 2,5-Dimethylpyrrole
(c) Triethylaluminium
(d) Hexachloroethane
PCE Perchloroethylene
C6 Aliphatic hydrocarbon having 6 carbon atoms The results in Table 7 and Table 8 verify that Examples 19 to 26 show increase in the content of the C6 component in the product and increase in the 1-hexene content contained in C6 while the catalyst activity is kept falling within an acceptable range, as compared with Comparative Example 7 where the supply of perchloroethylene (PCE) in the reactor is 0. However, when the supply of PCE to the reactor is increased to be up to 200 mol relative to the chromium catalyst (Comparative Example 8), the catalyst activity greatly lowers and it is known that any further improvement in the content of the C6 component in the product and also in the 1-hexene content contained in C6 could not be realized.

Example 27

The production was carried out in the same manner as Comparative Example 7, except that 161 ml of n-heptane, and 1.5 ml (0.055 mmol) of trichloroethylene diluted with n-heptane to be 5 g/L were supplied to the body of the autoclave. The molar ratio of the catalyst components, the molar ratio of trichloroethylene relative to the amount of the transition metal in the reaction step (in Table 9, molar ratio of TCE to (a)), and the results are shown in Table 9.

TABLE 9

|  | Ratio of Catalyst Components (molar ratio) (a)/(b)/(c)/(d) | Molar Ratio of TCE to (a) | Catalyst Activity [g/g-Cr] | C6 Component in Product [wt %] | 1-Hexene Contained in C6 [wt %] |
|---|---|---|---|---|---|
| Example 27 | 1/6/60/6 | 15 | 269000 | 93.2 | 99.0 |
| Comparative Example 7 | 1/6/60/6 | 0 | 297000 | 92.2 | 98.8 |

(a) Chromium(III)-2-ethylhexanoate
(b) 2,5-Dimethylpyrrole
(c) Triethylaluminium
(d) Hexachloroethane
TCE Trichloroethylene
C6 Aliphatic hydrocarbon having 6 carbon atoms The results in Table 9 verify that Example 27 show increase in the content of the C6 component in the product and increase in the 1-hexene content contained in C6 while the catalyst activity is kept falling within an acceptable range, as compared with Comparative Example 7 where the initial supply of trichloroethylene (TCE) in the reactor is 0.

While the invention has been described in detail and with reference to specific embodiments thereof, it will be apparent to one skilled in the art that various changes and modifications can be made therein without departing from the spirit and scope thereof. This application is based on Japanese patent applications filed on Feb. 25, 2014 (Application No. 2014-034394) and Mar. 24, 2014 (Application No. 2014-060711), the content thereof being incorporated herein by reference.

| Explanations of Reference Signs | |
|---|---|
| 10 | Reactor |
| 10a | Stirrer |
| 11, 22, 32, 41, 42, 51 | Line |
| 11a | Deactivator Supply Line |
| 12 | First Supply Line |
| 12a | Ethylene Supply Line |
| 13 | Second Supply Line |
| 13a | Catalyst Supply Line |
| 14 | Third Supply Line |
| 15 | Fourth Supply Line |
| 21, 31 | Circulation Line |
| 17 | Compressor |
| 20 | Degassing Tank |
| 30 | Ethylene Separation Tower |
| 40 | High-Boiling Separation Tower |
| 50 | Hexene Separation Tower |
| 52 | Solvent Circulation Line |

The invention claimed is:

1. A method for producing an α-olefin low polymer through low polymerization reaction of an α-olefin, the method comprising:
    reacting the α-olefin in the presence of a catalyst comprising a transition metal-containing compound, an aluminium-containing compound and a halogenated hydrocarbon having 2 or more carbon atoms and substituted with one or more halogen atoms, and a solvent, in a reactor, to produce a reaction product comprising an α-olefin low polymer, an unreacted α-olefin, a halogenated olefin having 2 or more carbon atoms and substituted with one or more halogen atoms, and solvent, wherein the halogenated olefin is a decomposed product of the halogenated hydrocarbon;
    purifying the reaction product to separate the α-olefin low polymer from the unreacted α-olefin, the halogenated olefin, and the solvent; and
    circulating the unreacted α-olefin, the halogenated olefin and the solvent to the reactor,
    wherein an amount of the circulated halogenated olefin relative to an amount of transition metal in the reactor is within a molar ratio range of from 1.0 to less than 200.

2. The method for producing an α-olefin low polymer according to claim 1, wherein the catalyst further comprises a nitrogen-containing compound.

3. The method for producing an α-olefin low polymer according to claim 1, wherein transition metal in the transition metal-containing compound is chromium.

4. The method for producing an α-olefin low polymer according to claim 1, wherein the α-olefin is ethylene and the α-olefin low polymer is 1-hexene.

5. The method for producing an α-olefin low polymer according to claim 1, wherein when the low polymerization reaction starts, an olefin having 2 or more carbon atoms and substituted with one or more halogen atoms, exists in a circulation line through which the halogenated olefin is circulated in an amount relative to the amount of the transition metal in the reactor that is within a molar ratio range of from 1.0 to less than 200.

6. The method for producing an α-olefin low polymer according to claim 1, wherein the amount of the halogenated olefin relative to the amount of the transition metal in the reactor is within a molar ratio range of from 1.0 to 170.

7. The method for producing an α-olefin low polymer according to claim 1, wherein the halogenated hydrocarbon is a hydrocarbon having 2 or more carbon atoms and substituted with 5 or more halogen atoms, and the halogenated olefin is an olefin having 2 or more carbon atoms and substituted with 3 or more halogen atoms.

8. The method for producing an α-olefin low polymer according to claim 1, wherein the halogenated hydrocarbon is 1,1,2,2-tetrachloroethane, and the halogenated olefin is 1,2-dichloroethylene.

9. The method for producing an α-olefin low polymer according to claim 1, wherein the halogenated hydrocarbon is hexachloroethane, and the halogenated olefin is perchloroethylene.

10. The method for producing an α-olefin low polymer according to claim 1, wherein the halogenated hydrocarbon is hexachloroethane, and the halogenated olefin is trichloroethylene.

11. The method for producing an α-olefin low polymer according to claim 1, wherein the halogenated hydrocarbon is perchloroethylene, and the halogenated olefin is trichloroethylene.

12. The method for producing an α-olefin low polymer according to claim 1, wherein an amount of the halogenated hydrocarbon relative to an amount of transition metal in the reactor is within a molar ratio range of from 0.5 to 50, and the amount of the circulated halogenated olefin relative to the amount of the halogenated hydrocarbon in the reactor is within a molar ratio range of 2 or more.

* * * * *